United States Patent
Kim et al.

(10) Patent No.: US 11,980,642 B2
(45) Date of Patent: May 14, 2024

(54) METHOD FOR EFFICIENTLY PRODUCING 3D MIDBRAIN-LIKE ORGANOID THROUGH SPECIFIC ELECTROMAGNETIC WAVE PROCESSING

(71) Applicant: DONGGUK UNIVERSITY INDUSTRY-ACADEMIC COOPERATION FOUNDATION, Seoul (KR)

(72) Inventors: Jongpil Kim, Seoul (KR); Junsang Yoo, Gyeonggi-do (KR)

(73) Assignee: DONGGUK UNIVERSITY INDUSTRY—ACADEMIC COOPERATION FOUNDATION, Seoul (KR)

( * ) Notice: Subject to any disclaimer, the term of this patent is extended or adjusted under 35 U.S.C. 154(b) by 652 days.

(21) Appl. No.: 16/470,584

(22) PCT Filed: Nov. 1, 2017

(86) PCT No.: PCT/KR2017/012235
§ 371 (c)(1),
(2) Date: Jun. 18, 2019

(87) PCT Pub. No.: WO2018/124450
PCT Pub. Date: Jul. 5, 2018

(65) Prior Publication Data
US 2020/0085879 A1 Mar. 19, 2020

(30) Foreign Application Priority Data
Dec. 26, 2016 (KR) ........................ 10-2016-0178992

(51) Int. Cl.
*A61K 35/30* (2015.01)
*C12N 5/079* (2010.01)
*C12N 13/00* (2006.01)

(52) U.S. Cl.
CPC ............ *A61K 35/30* (2013.01); *C12N 5/0618* (2013.01); *C12N 13/00* (2013.01); *C12N 2513/00* (2013.01); *C12N 2529/00* (2013.01)

(58) Field of Classification Search
CPC .. A61K 35/30; A61K 41/0023; C12N 5/0618; C12N 13/00; C12N 2513/00; C12N 2529/00; C12N 5/0619; G01N 2800/2821; G01N 33/5058; G01N 33/5073; G01N 33/5082; G01N 33/6896
See application file for complete search history.

(56) References Cited

U.S. PATENT DOCUMENTS

| | | | | |
|---|---|---|---|---|
| 2011/0070202 A1* | 3/2011 | Yarowsky | ............ | A61K 9/5115 424/93.7 |
| 2012/0076830 A1* | 3/2012 | Sitharaman | ............ | A61P 19/04 977/773 |
| 2013/0202565 A1* | 8/2013 | Park | ...................... | C12N 5/0618 424/93.7 |
| 2014/0322784 A1* | 10/2014 | Souza | .................... | C12N 13/00 435/173.1 |
| 2018/0334646 A1* | 11/2018 | Song | ...................... | C12M 21/08 |

FOREIGN PATENT DOCUMENTS

| | | |
|---|---|---|
| KR | 10-1472594 B1 | 12/2014 |
| WO | 2015-135893 A | 9/2015 |

OTHER PUBLICATIONS

Kim et al. "High-throughput generation of spheroids using magnetic nanoparticles for three-dimensional cell culture." Biomaterials . Nov. 2013;34(34):8555-63. (Year: 2013).*
Ma et al. "Extremely Low-Frequency Electromagnetic Fields Promote In Vitro Neuronal Differentiation and Neurite Outgrowth of Embryonic Neural Stem Cells via Up-Regulating TRPC1" PLoS One . Mar. 7, 2016;11(3):e0150923. (Year: 2016).*
Söderstjerna et al. "Gold- and silver nanoparticles affect the growth characteristics of human embryonic neural precursor cells," PLoS One .2013;8(3):e58211. (Year: 2013).*
Yang et al. "Comparisons of the biodistribution and toxicological examinations after repeated intravenous administration of silver and gold nanoparticles in mice."Scientific Reports vol. 7, Article No. 3303 (2017) (Year: 2017).*
Jadidi et al., "Mesenchymal stem cells that located in the electromagnetic fields improves rat model of Parkinson's disease," Iranian Journal of Basic Medical Sciences, Jul. 2016, vol. 19(7), pp. 741-748.
Jo et al., "Midbrain-like organoids from human pluripotent stem cells contain functional dopaminergic and neuromelanin-producing neurons," Cell Stem Cell, Aug. 4, 2016. vol. 19(2), pp. 248-257.
Baek et al., "Electromagnetic fields mediate efficient cell reprogramming into a pluripotent state," ACS Nano, 2014, vol. 8(10), pp. 10125-10138.
Choi et al., "Stimulation of Neural Differentiation in Human Bone Marrow Mesenchymal Stem Cells by Extremely Bone Marrow Mesenchymal Stem Cells by Extremely with MNPs," Appl Biochem Biotechnol, Oct. 2014, vol. 174(4), pp. 1233-1245.

* cited by examiner

*Primary Examiner* — Titilayo Moloye
(74) *Attorney, Agent, or Firm* — Riverside Law LLP (57) ABSTRACT

The present invention relates to a method of inducing differentiation into a 3D dopaminergic midbrain organoid using a specific electromagnetic wave. It was specifically identified that the method makes it possible to remarkably improve production efficiency of a dopaminergic neuronal 3D-differentiated organoid, from which symptoms of Parkinson's disease can be effectively alleviated. Thus, it is anticipated that the present invention is capable of making a more fundamental approach and achieving targeted therapies in the treatment of a cranial nerve disease.

5 Claims, 6 Drawing Sheets

METHOD FOR EFFICIENTLY PRODUCING 3D MIDBRAIN-LIKE ORGANOID THROUGH SPECIFIC ELECTROMAGNETIC WAVE PROCESSING

CROSS-REFERENCE TO RELATED APPLICATIONS

This application is the U.S. national phase application filed under 35 U.S.C. § 371 claiming benefit to International Patent Application No. PCT/KR2017/012235, filed on Nov. 1, 2017, which is entitled to priority under to Korean Patent Application No. 10-2016-0178992, filed Dec. 26, 2016, the disclosure of which is incorporated herein by reference in its entirety.

TECHNICAL FIELD

The present invention relates to a method of efficiently inducing differentiation into a 3D midbrain-like organoid containing dopaminergic neurons through treatment with a specific electromagnetic wave. More specifically, the present invention relates to a midbrain-like organoid produced by the method, and a method for screening a new drug and a cellular therapeutic agent using the same, the new drug and the cellular therapeutic agent being for the treatment of a cranial nerve disease.

BACKGROUND ART

In the treatment of cranial nerve diseases such as Alzheimer's disease, Parkinson's disease, cerebral infarction, cerebral hemorrhage, and spinal cord injury, a variety of new therapeutic candidates have been emerging through regeneration of neurons. As solutions associated with this, there have been developed various methods for treating a cranial nerve disease by administering patient-specific therapeutic cells made by using embryonic stem cells, totipotent stem cells, or the like. However, when such undifferentiated totipotent stem cells are transplanted, there is a risk of causing cancer. Thus, there is a limitation in utilization of such cells as a therapeutic agent.

In the latest stem cell technologies which have been developed recently, it has been found that it is possible to make an organoid structure in a 3D state having a structure similar to a body organ in a case where stem cells are differentiated into specific cells and differentiation into a 3D state is also induced in the process of differentiation of the stem cells into the specific cells. Based on these findings, the results that various miniature organoids such as brain organoids, heart organoids, liver organoids, lung organoids, and small intestine organoids can be produced have been reported so far.

The development of these organoids allows creation of a 3D environment close to an inside of the living body, which represents an advantage that not only can experiments be conducted as if a drug acts 'in vivo' even in 'ex vivo' experimental situations which could not be previously visualized, but also effects seen in actual human organs can be reproduced as they are. In addition, recently, it has been reported that even a midbrain organoid containing dopaminergic neurons can be produced. Such a midbrain organoid can be considered as a very effective way capable of replacing the system for modeling Parkinson's disease, and thus offers many possibilities in the future for verification of development of new drugs for the treatment of Parkinson's disease and development of new cell implants with low risk of carcinogenesis.

However, the biggest problem which is emerging at present is that it is reported that in the development of all organoids including such a 3D midbrain organoid, organoids can be induced only through a lot of time, treatments with various compounds in complicated steps, and the like. This inconvenience becomes a big challenge for the future use of 3D organoids. Accordingly, there is a need for a method capable of more efficiently producing organoids without complicated steps and various technical processing steps in and out of the living body (see Korean Laid-Open Patent Publication No. 10-2012-0003855).

DISCLOSURE

Technical Problem

The present invention has been conceived to solve the problems as described above. The present inventors have found that when stem cells are treated with a specific electromagnetic wavelength having a certain frequency which is capable of inducing a 3D midbrain structure in the stem cells, a 3D midbrain organoid can be more efficiently produced. Base on this finding, the present inventors have completed the present invention.

Accordingly, an object of the present invention is to provide a method of inducing differentiation into a 3D midbrain-like organoid, comprising a step of applying an electromagnetic field to stem cells.

Another object of the present invention is to provide a cellular therapeutic agent for treating a cranial nerve disease, comprising a neuron differentiated by the method.

However, the technical problems to be solved by the present invention are not limited to the above-mentioned problems, and other problems not mentioned can be clearly understood by those skilled in the art from the following description.

Technical Solution

In order to achieve the objects as described above, the present invention provides a method of inducing differentiation into a 3D midbrain-like organoid, comprising a step of applying an electromagnetic field to stem cells.

In an embodiment of the present invention, the method may further comprise a step of contacting the stem cells with metal nanoparticles.

In another embodiment of the present invention, the electromagnetic field may be applied at an intensity of 5 Gauss to 100 Gauss.

In yet another embodiment of the present invention, the electromagnetic field may be applied at a frequency of 10 Hz to 500 Hz.

In still yet another embodiment of the present invention, the metal nanoparticles may be any one selected from the group consisting of gold nanoparticles, silver nanoparticles, and magnetic nanoparticles.

In still yet another embodiment of the present invention, the stem cells may be mesenchymal stem cells, induced pluripotent stem cells, pluripotent stem cells, or neural stem cells.

In addition, the present invention provides a cellular therapeutic agent for treating a cranial nerve disease, comprising the 3D midbrain-like organoid differentiated by the method.

In an embodiment of the present invention, the cranial nerve disease may be any one selected from the group consisting of Alzheimer's disease, Parkinson's disease, cerebral infarction, cerebral hemorrhage, and stroke.

In addition, the present invention provides a method for treating a cranial nerve disease, comprising a step of administering the cellular therapeutic agent to a subject.

In addition, the present invention provides a use of a neuron differentiated by the method, in the preparation of a therapeutic agent for a cranial nerve disease.

In addition, the present invention provides a method for treating a brain cranial disease, comprising a step of transplanting, into a subject, the 3D midbrain-like organoid differentiated by the method.

In addition, the present invention provides a method for screening a therapeutic agent for a cranial nerve disease, using the 3D midbrain-like organoid differentiated by the method.

Advantageous Effects

The present invention relates to a method of inducing differentiation into a 3D dopaminergic midbrain organoid using a specific electromagnetic wave. The method makes it possible to remarkably improve production efficiency of a dopaminergic neuronal 3D-differentiated organoid, and makes it possible to efficiently implement a 3D development model of Parkinson's disease, which was difficult to implement in existing models, by providing a 3D environment that can create a structure similar to existing brain tissue in a more effective manner than existing stem cells. In addition, it has been specifically identified that a 3D midbrain structure can maximize a cell regeneration effect, thereby effectively alleviating symptoms of Parkinson's disease. Thus, it is expected that the method can be usefully used as a technique for treating a cranial nerve disease.

Such a 3D-based technique for producing an organoid using treatment with an electromagnetic field can lead to production of an organoid in a non-invasive, simple, and efficient manner using a physical electromagnetic field. In addition, even when the production of the organoid is completed, the present technique has an advantage capable of regulating production effects of 3D neurons for transplantation depending on a degree of development by simply eliminating treatment with an electromagnetic field.

MODES OF THE INVENTION

The present inventors have identified that it is possible to remarkably enhance production efficiency of a 3D midbrain-like organoid by treatment with a specific electromagnetic wave, and to freely regulate 3D differentiation capacity thereof by regulating a condition of an electromagnetic field applied in this process. In addition, the present inventors have applied this method in vivo, and have also specifically found the enhancement of differentiation efficiency into 3D midbrain neurons and the effects of alleviating symptoms in an experiment using an animal model of Parkinson's disease. Based on this finding, the present inventors have completed the present invention.

Hereinafter, the present invention will be described in detail.

The present invention provides a method of inducing differentiation into a 3D midbrain-like organoid, comprising a step of applying an electromagnetic field to stem cells.

As used herein, the term "stem cells" refers to 'undifferentiated' cells having an ability to differentiate into various types of body tissues, meaning all types of stem cells including embryonic stem cells or adult stem cells.

As used herein, the term "organoid" refers to a 'miniature pseudo-organ' which is made by using stem cells to be able to perform a minimal function, and has a feature of being made in a three-dimensional structure and capable of creating an environment similar to an actual body organ even in a laboratory.

As used herein, the term "3D midbrain-like organoid" refers to a miniature pseudo-organ obtained by creating, in a small scale, the 'midbrain' that is a part of the brain, and has a feature of possessing actions which occur in the human brain as they are, in that neurons are connected to form a network, and transmit signals to each other and produce neurotransmitters, and the like.

In an embodiment of the present invention, in order to enhance differentiation efficiency into the 3D midbrain-like organoid, stem cells were brought into contact with metal nanoparticles, and then an electromagnetic field was applied to induce electromagnetism in the metal nanoparticles; and metal nanoparticles and related transcription factors were injected together into the brain which was within an animal body, and then the animal was directly applied to application of an electromagnetic field.

In the present invention, the electromagnetism-induced metal nanoparticles promote differentiation of the stem cells into an organoid, and may be preferably, but are not limited to, gold, silver, or magnetic nanoparticles.

In addition, the electromagnetic field may be applied at an intensity of 5 Gauss to 50 Gauss and/or a frequency of 10 Hz to 500 Hz, and may be preferably, but is not limited to, an electromagnetic field of 10 Gauss/100 Hz.

Accordingly, the present invention provides a cellular therapeutic agent for treating a cranial nerve disease, comprising a 3D midbrain-like organoid differentiated by the method.

As used herein, the term "treatment" means any action that ameliorates or beneficially alters symptoms of a cranial nerve disease by administration of a pharmaceutical composition or cellular therapeutic agent of the present invention.

"Cranial nerve disease", which is a disease to be treated according to the present invention, collectively refers to various diseases related to nerves, in particular, cranial nerves, and may be preferably, but is not limited to, Alzheimer's disease, Parkinson's disease, cerebral infarction, cerebral hemorrhage, stroke, or a spinal cord injury disease, with Parkinson's disease being more preferred.

In the present invention, "cellular therapeutic agent" refers to a pharmaceutical used for the purpose of treatment, diagnosis, and prevention, which contains cells and tissues prepared by isolation from a human, culture, and special manipulation, the pharmaceutical being used for the purpose of treatment, diagnosis, and prevention through a series of actions ex vivo, such as performing proliferation and selection of living autologous, allogeneic, or xenogeneic cells, or otherwise altering biological characteristics of the cells, in order to restore functions of cells or tissues.

Meanwhile, in another aspect of the present invention, there is provided a method for treating a cranial nerve disease, comprising a step of administering the cellular therapeutic agent to a subject.

In the present invention, "a subject" means a subject in need of treatment of a disease, and more specifically means a mammal such as a human or non-human primate, a mouse, a rat, a dog, a cat, a horse, and a cow.

Hereinafter, preferred examples will be described in order to facilitate understanding of the present invention. However, the following examples are provided only for the purpose of easier understanding of the present invention, and the present invention is not limited by the following examples.

Figure 1:
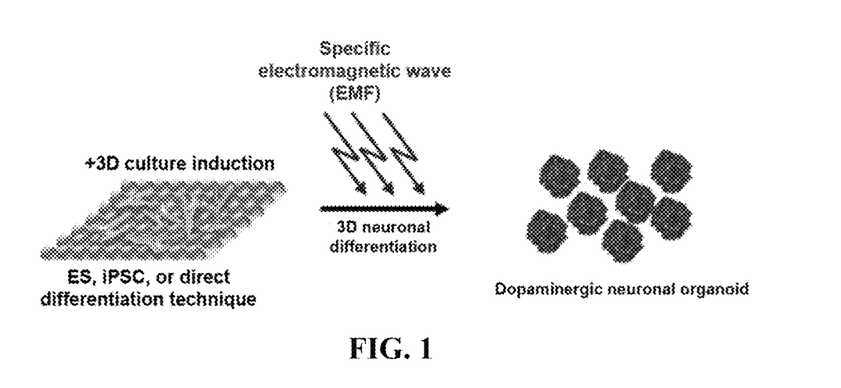
FIG. 1 illustrates a schematic diagram showing a process of producing a 3D midbrain-like organoid by performing treatment with a specific electromagnetic wave (10 Gauss, 100 Hz) of the present invention.

Example 1. Induction of Efficient Differentiation into 3D Dopaminergic Neuronal Organoid Using Electromagnetic Field In order to identify a method capable of more efficiently inducing differentiation of stem cells into a 3D dopaminergic neuronal organoid, a method of subjecting stem cells including embryonic stem cells and induced pluripotent stem cells to treatment with a specific electromagnetic field to differentiate into a 3D neuronal organoid was contemplated, which is schematically shown in FIG. 1. More specifically, it was confirmed whether efficiency of differentiation into a 3D dopaminergic neuronal organoid is enhanced depending on various intensities and wavelengths of an external electromagnetic field.

1-1. Changes in Differentiation Efficiency of 3D Neuronal Organoid Depending on Intensity of Electromagnetic Field First, in order to evaluate activity of differentiation into a 3D dopaminergic neuronal organoid depending on changes in treatment (intensity) with an electromagnetic field, electromagnetic fields of various intensities (3 to 100 Gauss) were applied, and then the size of dopaminergic neuronal organoids which had been produced through 3D culture from stem cells was identified. More specifically, for the respective pluripotent embryonic and induced pluripotent stem cells, differentiation was induced through 3D culture under an electromagnetic field of 10 Gauss for about 12 days, and efficient production of a dopaminergic neuronal organoid was identified through measurement of the diameter thereof. Here, three independent 3D differentiation induction experiments were performed with human embryonic stem cells, and three independent 3D differentiation induction experiments were also performed with human induced pluripotent stem cells. The mean value and standard deviation of the results obtained by measuring the resulting diameters were identified.

Figure 2:
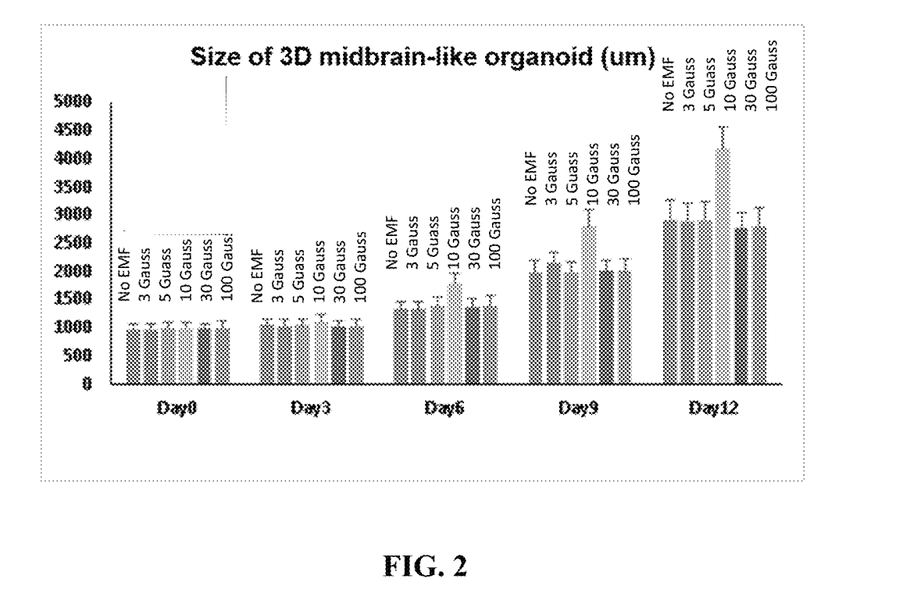
FIG. 2 illustrates the results obtained by comparing changes in size of a 3D midbrain-like organoid under a specific electromagnetic wave (10 Gauss, 100 Hz) of the present invention with those under electromagnetic waves having various intensities (3, 5, 10, or 30 Gauss).

As a result, as illustrated in FIG. 2, it was identified that a dopaminergic neuronal organoid was efficiently produced under a condition of 10 Gauss when treatment with an electromagnetic wave of 10 Gauss was performed for 12 days.

In addition, in order to further verify the results, the number of dopaminergic neuronal organoids expressing tyrosine hydroxylase (TH) and class III β-tubulin (Tuj1) which are neuron indicator genes was measured. Here, three independent differentiation experiments were performed with embryonic stem cells and three independent differentiation experiments were performed with induced pluripotent stem cells. The produced dopaminergic neuronal organoids were immunostained, and then the total number thereof was measured under fluorescence microscopy. Identification was achieved through the mean value and standard deviation of the obtained results.

Figure 3:
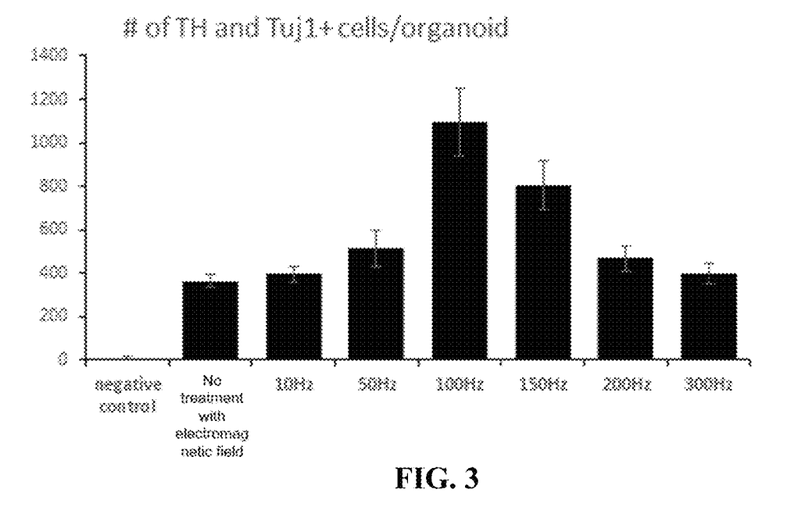
FIG. 3 illustrates a graph showing the number of positive dopaminergic neurons that commonly display TH and Tuj1 in 3D midbrain-like organoids produced by performing treatment with electromagnetic waves of several frequencies (10, 50, 100, 150, 200, or 300 Hz) for 7 days.

As a result, as illustrated in FIG. 3, it was identified that a dopaminergic neuronal organoid was produced in the maximum amount under a condition of 10 Gauss when treatment with an electromagnetic wave of 10 Gauss was performed for 7 days.

1-2. Changes in Differentiation Efficiency of 3D Neuronal Organoid Depending on Wavelengths of Electromagnetic Field Next, in order to evaluate activity of differentiation into a 3D dopaminergic neuronal organoid depending on changes in wavelength of an electromagnetic field, electromagnetic fields of various wavelengths (50, 100, 150, and 250 Hz) were applied, and then changes in the number of dopaminergic neuronal organoids which are TH+/Tuj1+ were measured and compared. Here, three independent 3D differentiation induction experiments were performed with embryonic stem cells, and three independent 3D differentiation induction experiments were also performed with induced pluripotent stem cells. The produced dopaminergic neuronal organoids were immunostained, and then the number of TH+/Tuj1+ dopaminergic neuronal organoids was measured. Identification was achieved through the mean value and standard deviation of the obtained results.

Figure 4:
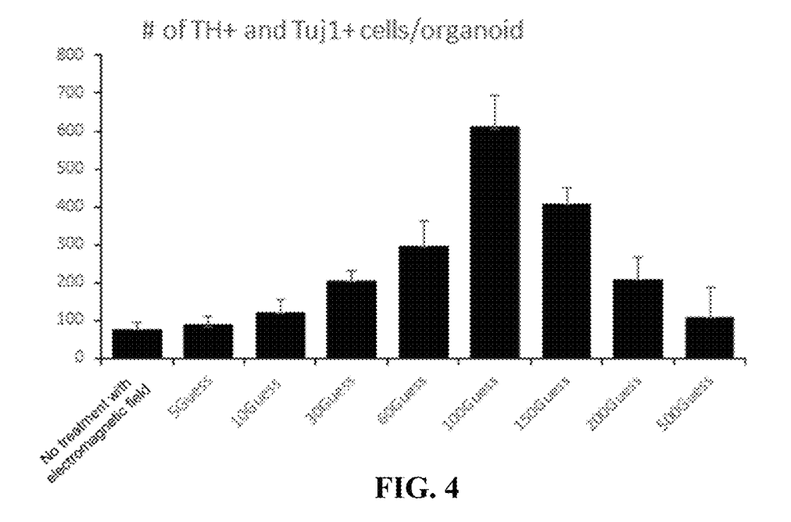
FIG. 4 illustrates a graph showing the number of positive dopaminergic neurons that commonly display TH and Tuj1 in 3D midbrain-like organoids produced by performing treatment with electromagnetic waves of several intensities (10, 30, 60, 100, 150, 200, or 500 Gauss) for 7 days.

As a result, as illustrated in FIG. 4, a large number of TH+/Tuj1+ dopaminergic organoids were measured in the group to which an electromagnetic field had been applied as compared with the group to which no electromagnetic field had been applied. In particular, it was identified that the largest number of TH+/Tuj1+ dopaminergic neuronal organoids were produced in the group to which an electromagnetic field of 100 Hz had been applied when the induced pluripotent and embryonic stem cells were differentiated in a 3D state.

1-3. Identification of Efficiency of Differentiation of 3D Neuronal Organoid Depending on Treatment with Specific Electromagnetic Field For further validation of the electromagnetic wave-treated 3D organoids produced by the above-described method, in dopaminergic neuronal organoids produced by treatment with an electromagnetic field of 10 Gauss and 100 Hz for 7 days, the degree of expression of TH and synapsin, known as markers for mature dopaminergic neurons, was compared quantitatively by RT-PCR analysis (real time PCR analysis). Here, as a control group, the group to which an electromagnetic field had not been applied or the group in which differentiation had been induced by being attached to a plate in a 2D state was used and compared. Three independent, respective 2D and 3D differentiation induction experiments were performed with embryonic stem cells, and three independent, respective 2D and 3D differentiation induction experiments were performed with induced pluripotent stem cells. The produced dopaminergic neuronal organoids were subjected to RT-PCR, and then the relative difference in amounts of expression obtained was identified by the mean value and standard deviation (Diff medium: differentiation is induced by a differentiation induction medium; EMF: treatment with an electromagnetic field is performed).

Figure 5:
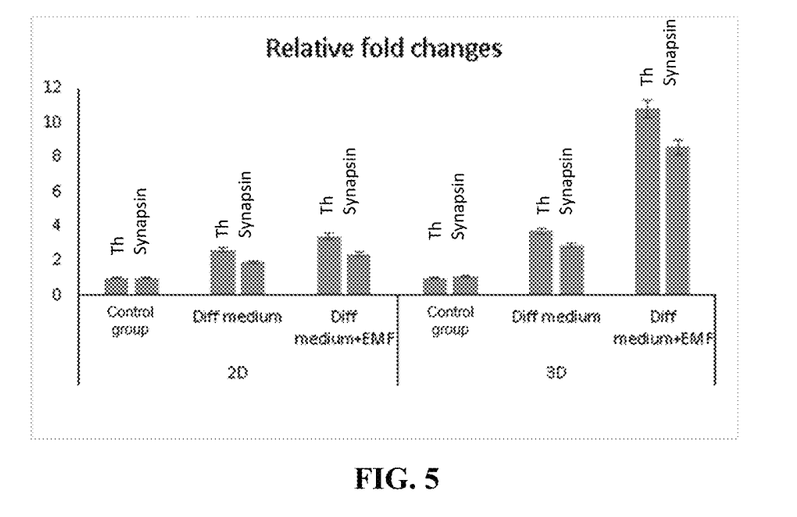
FIG. 5 illustrates a graph showing the expression of Th and synapsin, which are dopaminergic neuron genes, under a condition of 10 Gauss/100 Hz when real time qPCR is performed in 2D and 3D, respectively.

As a result, as illustrated FIG. 5, it was found that the expression of TH and synapsin, which are mature dopaminergic neuron indicator genes, was significantly increased only in the group to which an electromagnetic field having an intensity of 10 Gauss and a wavelength of 100 Hz had been applied in a 3D differentiation state, as compared with the control group.

In addition, in order to additionally confirm the above results, organoids, which had been produced through a 3D differentiation from induced pluripotent and embryonic stem cells while performing treatment with an electromagnetic wave for 7 days, were fixed (4% PFA fixation), and then tissues were exfoliated at 7 μm. The number of dopaminergic neurons in the organoid tissue was measured. In order to identify dopaminergic neurons, dopaminergic neurons present in one organoid were immunostained through MAP2 and TH antibodies. Here, three independent 3D differentiation induction experiments were performed with embryonic stem cells, and three independent 3D differentiation induction experiments were also performed with induced pluripotent stem cells. Five tissues were prepared from each of the produced dopaminergic neuronal organoids and immunostaining was performed. Tissues obtained through the staining from the five organoids were randomly selected, and counting in each field was performed. Then, the mean value and standard deviation of the number of the obtained Map2+/TH+ neurons were identified.

Figure 6A:
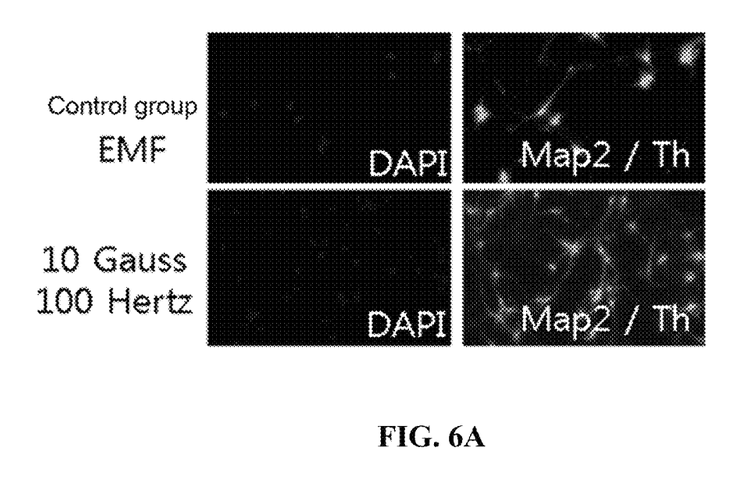
FIG. 6A illustrates the results obtained by performing immunostaining in 2D and 3D under an electromagnetic wave condition of 10 Gauss/100 Hz.
Figure 6B:
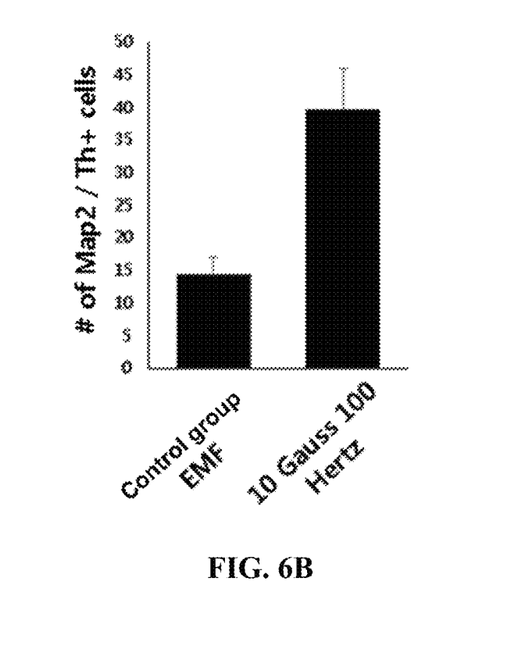
FIG. 6B illustrates the results obtained by quantifying the immunostaining.

As a result, as illustrated in FIGS. 6A and 6B, the largest number of Map2+/TH+ were observed in the dopaminergic neuronal organoid tissue made in the group to which an electromagnetic field of 10 Gauss and 100 Hz had been applied.

Figure 7:
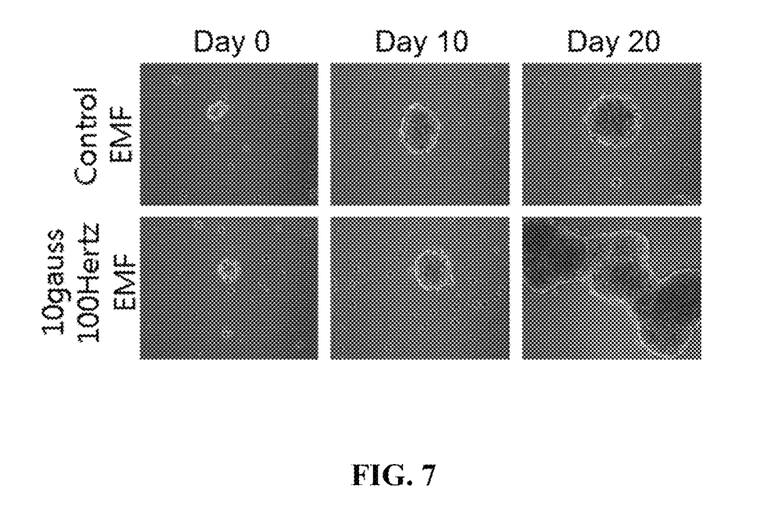
FIG. 7 illustrates cells differentiated into a 3D midbrain-like organoid by treatment with a specific electromagnetic wave (10 Gauss, 100 Hz) of the present invention.

Taken together, it was found that the optimal dopaminergic neuronal organoid was produced when treatment with an electromagnetic wave having an intensity of 10 Gauss and a wavelength of 100 Hz was performed. In addition, based on these results, it was additionally found that a dopaminergic neuronal organoid having a remarkably larger size was formed in the group to which an electromagnetic field had been applied as compared with the control group when a 3D differentiation into dopaminergic neurons was induced through treatment with an electromagnetic wave of 10 Gauss and 100 Hz wavelength for up to 20 days (see FIG. 7).

Example 2. Identification of Increased Production Efficiency of 3D Dopaminergic Neuronal Organoid Utilizing Metal Nanoparticles Magnetized with Electromagnetic Field In the present example, based on the results of the above examples, an attempt was made to identify whether addition of metal nanoparticles to maximize the effect due to treatment with an electromagnetic field can more efficiently enhance induction of differentiation into a 3D dopaminergic neuronal organoid. More specifically, an attempt was made to identify that in a case where stem cells are first treated with gold nanoparticles (in which the gold nanoparticles have been coated with an RGD protein so that the gold nanoparticles are easily adsorbed on the cell surface when the cells are treated therewith) and then an electromagnetic field is applied, the metal nanoparticles are more directly magnetized in the cells, thereby more efficiently inducing 3D differentiation into a dopaminergic neuronal organoid. As a control group, a group (control) for which no treatment with metal nanoparticles or electromagnetic field had been performed was used. Here, three independent 3D differentiation induction experiments were performed with embryonic stem cells, and three independent 3D differentiation induction experiments were also performed with induced pluripotent stem cells. Four tissues were randomly selected from each of the produced dopaminergic neuronal organoids and immunostaining was performed. In each organoid, identification was achieved through the mean value and standard deviation of the number of Tuj1+/TH+ cells found in any tissue obtained through the staining (EMF: treatment with an electromagnetic field, AuNPs: gold nanoparticles).

Figure 8:
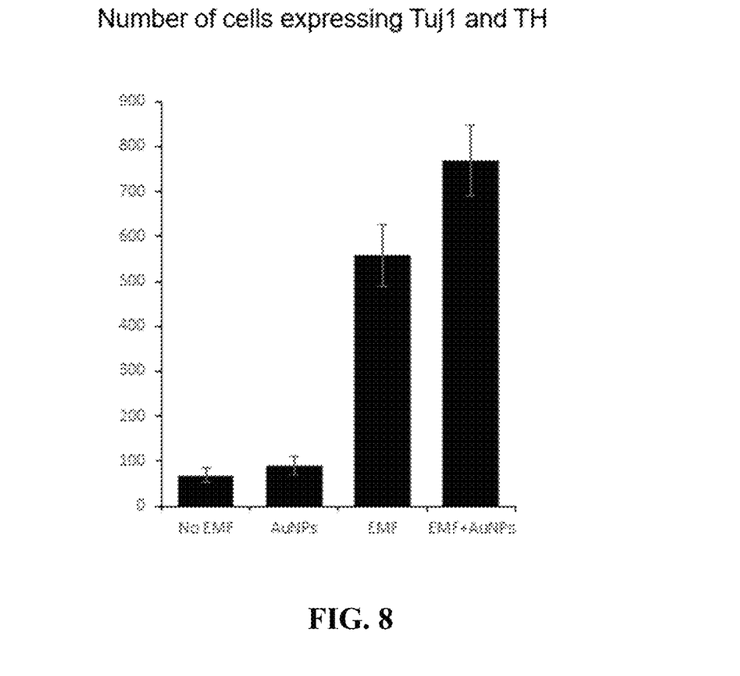
FIG. 8 illustrates a graph identifying that more 3D dopaminergic neurons are generated than a control group when treated together with metal nanoparticles (gold nanoparticles) under a condition of applying or not applying an electromagnetic wave of 10 Gauss/100 Hz.

As a result, as illustrated in FIG. 8, it was found that in a case where stem cells are treated with gold nanoparticles and then an electromagnetic field of 10 Gauss and 100 Hz is applied for 7 days, the number of cells expressing Tuj1 and TH which are neural indicator genes is increased in an electromagnetized dopaminergic neuronal organoid.

Example 3: Identification of Therapeutic Effect on Parkinson's Disease Utilizing 3D Neuronal Organoid Differentiated by Using Electromagnetic Field Furthermore, in the present example, an attempt was made to identify in vivo a therapeutic effect of the organoid, which had been induced to differentiate into a 3D neuronal organoid produced in the present invention, using an animal model of Parkinson's disease. For this purpose, a 3D dopaminergic neuronal organoid, which had been differentiated by the method of Example 1 for 7 days under an electromagnetic field, was transplanted into the brain of mice of Parkinson's disease, of which only one side of the brain had been treated with 6-hydroxydopamine (6-OHDA), and behavioral properties of the mice were analyzed. Here, as a control group, an organoid produced in the group to which an electromagnetic field had not been applied was used for transplantation. Three independent 3D differentiation induction experiments were performed with embryonic stem cells and three independent 3D differentiation induction experiments were also performed with induced pluripotent stem cells. Each of the produced dopaminergic neuronal organoids were transplanted into a mouse model of Parkinson's disease which had been produced by treating 5 animals each with 6-OHDA. Three weeks after the transplantation, apomorphine was utilized to induce rotation for 30 minutes, and the behavior results were quantified to identify the mean value and standard deviation.

Figure 9:
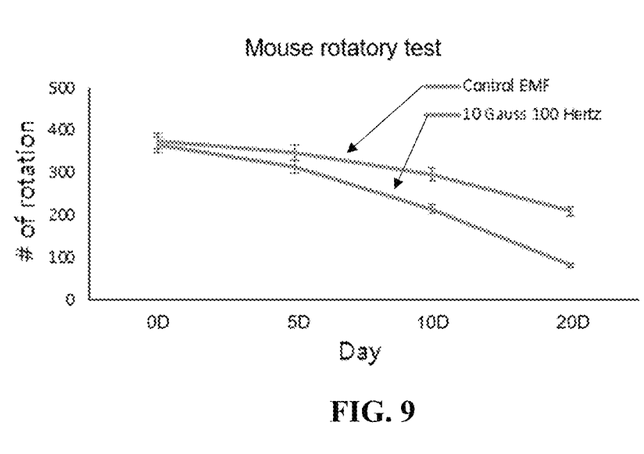
FIG. 9 is a graph identifying a therapeutic effect on Parkinson's disease through behavioral experiments in an MPTP animal model of Parkinson's disease, after being transplanted with a midbrain organoid produced by applying a specific electromagnetic wave (10 Gauss, 100 Hz).

As a result, as illustrated in FIG. 9, when mice are treated with 6-hydroxydopamine (6-OHDA) in only one side of the brain, due to necrosis of dopaminergic neurons in the one side, the mice generally showed a rotational behavior pattern, whereas when an electromagnetic field-treated organoid was transplanted into mice, the mice showed efficiently less rotational behavior than the control group. This confirmed that the electromagnetic field-treated 3D dopaminergic neurons are also effective in cell therapy.

Taken together, it can be seen that the 3D dopaminergic neuronal organoid produced through the method of the present invention exerts a more effective effect in cell therapy, and thus it is expected that the present invention can be used as a technique for treating a degenerative cranial nerve disease.

It will be understood by those skilled in the art that the foregoing description of the present invention is for illustrative purposes only and that various changes and modifications may be made easily without departing from the spirit or essential characteristics of the present invention. Therefore, it should be understood that the above-described examples are illustrative in all aspects and not restrictive.

INDUSTRIAL APPLICABILITY

The differentiation method proposed in the present invention makes it possible to remarkably improve production efficiency of a dopaminergic neuronal 3D-differentiated organoid, makes it possible to efficiently implement a 3D development model of Parkinson's disease, which was difficult to implement in existing models, by providing a 3D environment that can create a structure similar to existing brain tissue in a more effective manner than existing stem cells, and allows symptoms of Parkinson's disease to be effectively alleviated by maximizing a cell regeneration effect through a 3D midbrain structure. Thus, the present invention can be usefully used in the field of treating a cranial nerve disease.

In addition, such a 3D-based technique for producing an organoid using treatment with an electromagnetic field can lead to production of an organoid in a non-invasive, simple, and efficient manner using a physical electromagnetic field. Even when the production of the organoid is completed, it is possible to regulate production effects of 3D neurons for transplantation depending on a degree of development by simply eliminating treatment with an electromagnetic field. Thus, the present invention can be usefully used in the field of application of organoids.

The invention claimed is:

1. A method of inducing differentiation of stem cells into a 3D dopaminergic midbrain organoid, comprising:
   a step of contacting the stem cells with gold nanoparticles coated with an RGD protein; and
   a step of applying an electromagnetic field to the stem cells to induce differentiation of the stem cells into a 3D dopaminergic midbrain organoid, thereby obtaining the 3D dopaminergic midbrain organoid,
   wherein the stem cells are one or more selected from the group consisting of embryonic stem cells and induced pluripotent stem cells,
   wherein the electromagnetic field is applied at an intensity of 10 Gauss and at a frequency of 100 Hz for 7 days, and
   wherein the 3D dopaminergic organoid expresses two or more markers selected from the group consisting of Th, Tuj1, and Synapsin.

2. A cellular therapeutic agent for treating cranial nerve disease, comprising:
   the 3D dopaminergic midbrain organoid obtained by the method according to claim 1.

3. The cellular therapeutic agent according to claim 2, wherein the cranial nerve disease is any one selected from the group of Alzheimer's disease, Parkinson's disease, cerebral infarction, cerebral hemorrhage, and a spinal cord injury disease.

4. A method for treating a cranial nerve disease comprising:
   a step of administering, to a subject, the cellular therapeutic agent according to claim 2.

5. A method for treating a cranial nerve disease comprising:
   a step of transplanting, into a subject, the 3D dopaminergic midbrain organoid obtained by the method according to claim 1.

* * * * *